(12) United States Patent
Gruber et al.

(10) Patent No.: US 6,664,284 B2
(45) Date of Patent: Dec. 16, 2003

(54) STABILIZED CARVEDILOL INJECTION SOLUTION

(75) Inventors: Werner Gruber, Birkenau (DE); Heinrich Woog, Laudenbach (DE)

(73) Assignee: Roche Diagnostics GmbH, Mannheim (DE)

( * ) Notice: Subject to any disclaimer, the term of this patent is extended or adjusted under 35 U.S.C. 154(b) by 23 days.

(21) Appl. No.: 10/136,938

(22) Filed: May 1, 2002

(65) Prior Publication Data

US 2002/0169199 A1 Nov. 14, 2002

Related U.S. Application Data

(63) Continuation of application No. 09/743,671, filed as application No. PCT/EP99/04974 on Jul. 14, 1999, now abandoned.

(30) Foreign Application Priority Data

Jul. 23, 1998 (DE) .......................................... 198 33 119

(51) Int. Cl.[7] ............................................ A61K 31/403
(52) U.S. Cl. ....................................................... 514/411
(58) Field of Search .......................................... 514/411

(56) References Cited

U.S. PATENT DOCUMENTS

| | | | |
|---|---|---|---|
| 4,503,067 A | | 3/1985 | Wiedemann et al. |
| 5,071,868 A | * | 12/1991 | Leinert ........................ 514/411 |
| 5,308,862 A | | 5/1994 | Ohlstein |

FOREIGN PATENT DOCUMENTS

| | | |
|---|---|---|
| WO | WO 96/24348 | 8/1996 |

OTHER PUBLICATIONS

Yue, et al., The Journal of Pharmacology & Experimental Therapeutics (1992), vol. 236 (1), pgs. 92–98.

J. Cardiovas. Pharmacology, 1992, vol. 19 (Suppl 1), pgs. S62–S67.

* cited by examiner

*Primary Examiner*—Phyllis G. Spivack
(74) *Attorney, Agent, or Firm*—George W. Johnston; Patricia S. Rocha-Tramaloni; Bernard Lau

(57) ABSTRACT

Ready-to-use, aqueous injection solutions containing carvedilol (1-(9H-carbazolyl-4-yloxy)-3-[[(2-(2-methoxyphenoxy)ethyl]-amino]-2-propanol) or its pharmacologically harmless salts which are stable in storage and are well tolerated by veins are disclosed.

15 Claims, No Drawings

STABILIZED CARVEDILOL INJECTION SOLUTION

CROSS REFERENCE TO RELATED APPLICATION

This is a continuation of patent application Ser. No. 09/743,671 filed Jan. 10, 2001 now abandoned, which is a 371 of PCT/EP99/04974 filed Jul. 14, 1999.

The object of the invention are ready-to-inject, aqueous injection solutions containing carvedilol (1-(9H-carbazol-4-yloxy)-3-[[2-(2-methoxyphenoxy)ethyl]amino]-2-propanol) or its pharmacologically harmless salts as well as a process for their production. The injection solutions are stable on storage and are tolerated well by veins.

Carbazol-4-yloxy-propanolamine derivatives as well as their pharmacologically harmless salts, which exhibit vasodilating and β-receptor blocking activities in pharmacological tests and which are suitable for the treatment and prophylaxis of circulatory and cardiac disorders such as hypertension and angina pectoris, are known from EP 0 004 920.

Carvedilol and carvedilol derivatives are also described by Yue et al. in "The Journal of Pharmacology and Experimental Therapeutics" 236 (1), pages 92–98 (1992). The authors report that carvedilol and especially carvedilol derivatives which are hydroxylated in the carbazole structure or in the phenoxy ring exhibit an antioxidative activity and inhibit lipid peroxidation.

Although enteral, parenteral and oral dosage forms are proposed in EP 0 004 920, only oral dosage forms have hitherto been developed successfully. There has, indeed, been a series of experiments to incorporate carvedilol into conventional injectable preparations. However, these have hitherto surprisingly come to nothing. It has been found that such preparations are either not tolerated by veins or are not sufficiently stable, so that in the case of lengthy storage the solutions recrystallize or decomposition products are formed. These negative phenomena thus exclude use for injection purposes.

The solubility of carvedilol in water is about 0.2 mg/100 ml, i.e. 0.002 mg/ml, with a pH value of 6.1 resulting. This solubility is, of course, not sufficient to achieve the therapeutically required dosage of an injection solution in the order of several mg/ml. Upon standing, supersaturated solutions precipitate carvedilol crystals after a short period, so that they are unsuitable as ready-to-inject injection solutions. An increase in the acidity to pH values of 1 to 3 indeed prevents the crystallization of the carvedilol and increases the dissolved amount of the active substance, but leads to an intolerance of the solutions by veins. Moreover, decomposition products form therefrom after a short period. These decomposition products also mean that such a solution can not be used for injection purposes.

Long-term medication with carvedilol has accordingly hitherto been carried out predominantly in the form of solid dosage forms such as tablets and capsules. It would, however, also be desirable, especially for clinical uses, to provide readily injectable dosage forms. In order, in use, not to have to rely on the necessity of firstly mixing the components with one another, e.g. in the case of a lyophilizate, such an injection solution should be as "ready-to-inject" as possible. In other words, all required components should already be present in the correct ratios in the ampoule solution.

The object of the invention was to find a formulation in order to provide carvedilol or its pharmacologically harmless salts as injection solutions having therapeutically relevant concentrations, with the injection solutions being stable on storage and being tolerated well by veins.

Surprisingly, stable, vein-tolerable and high dosage injection solutions containing carvedilol or its pharmacologically harmless salts are obtained when on the one hand a physiologically compatible acidic buffer having a pH value between 7.2 and 4.0 and on the other hand an organic solvent, such as, for example, polyethylene glycol, is added to the solution. It is also necessary to add an antioxidant and an agent which binds metal ions.

The ready-to-inject injection solutions containing carvedilol or its pharmacologically harmless salts in accordance with the invention contain a physiologically compatible buffer having a pH value of 7.2 to 4.0, a water-soluble organic solvent, an antioxidant as well as an agent which binds heavy metals.

The carvedilol concentration in the ready-to-inject injection solutions is preferably 1 to 5 mg/ml.

Examples of pharmacologically harmless salts are salts of carvedilol with inorganic or organic acids, such as e.g. hydrochloric acid, hydrobromic acid, phosphoric acid, sulphuric acid, acetic acid, citric acid, maleic acid or benzoic acid.

The injection solutions in accordance with the invention have a pH value of 4.0 to 7.4, preferably from 4.4 to 7.0.

Amounts of active substance and adjuvants are chosen such that isotonic injection solutions are obtained as far as possible. In the event that this is not already guaranteed by the available components, other adjuvants which are customary for this purpose, such as e.g. sodium chloride, fructose, glucose etc., can also be added to adjust the isotonicity.

Organic solvents which are preferably used are ethanol and solvents which have a degree of polymerization. Solvents which have a degree of polymerizaton in accordance with the invention are preferably trimethylene glycol and polyethylene glycol. Polyethylene glycol with a molecular weight between 100 and 1,500, particularly 200 to 600, has been found to be especially preferred. The organic solvent is usually added in an amount of 5 to 25 wt. %, with an addition of about 10 wt. % being preferred.

Physiologically compatible buffer substances in accordance with the invention are, for example, weak acids, such as acetic acid, malic acid, carbonic acid, phosphoric acid or amino acids. In particular, the sodium, potassium or ammonium salts of the acids such as the acetate, malate, carbonate, phosphate, glycinate, arginate or other amino acid salts come into consideration.

A special case of buffering comprises adding a further active substance which acts as a buffer to the aforementioned buffers. As the carvedilol injection solutions in accordance with the invention are stable in the acidic to neutral range, there exists the possibility of incorporating a loop diuretic in the formulations in addition to the β-blocker carvedilol. Torasemide, azosemide and furosemide are preferably used as loop diuretics, and in these aqueous injection solutions the organic solvents such as polyethylene glycol, trimethylene glycol or ethanol can be present in a maximum amount of 25%. The solubility of the loop diuretics in these acidic to maximum neutral formulations is as follows:
Torasemide from 1 mg/ml to 2 mg/ml
azosemide from 1 mg/ml to 3 mg/ml
furosemide from 1 mg/ml to 5 mg/ml The furosemide, torasemide or azosemide is preferably added in the form of the sodium or potassium salt.

Preferred buffer substances present in the ready-to-inject injection solutions are sodium, potassium or ammonium salts of weak acids and/or loop diuretics or their sodium or potassium salts, with torasemide, azosemide or furosemide being especially preferred as the loop diuretic.

As the antioxidant there can be used any additive which is effective in an acidic medium and which is suitable for injection solutions, e.g. inorganic or organic sulphur compounds, such as e.g. methionine or sodium disulphide, or ascorbic acid in the form of sodium ascorbate. Methionine is preferably used in accordance with the invention, especially in a concentration of 1 to 10 mg/ml, preferably of 2 to 5 mg/ml.

The optimal stabilization of the formulation is guaranteed surprisingly by an agent which binds heavy metal ions, such as e.g. a complex former which inactivates heavy metal ions, preferably EDTA (ethylenediaminetetraacetic acid, edetic acid) or its disodium salt (Titriplex III). It has surprisingly been found that the solvent-containing carvedilol solutions are only sufficiently stable and endure a sterilization for 20 minutes in the final container at 121° C. without decomposition when the combination of antioxidant and heavy metal ion binder is guaranteed. The concentration of the complex former is 0.1 to 10 mg/l, preferably 0.1 to 0.3 mg/ml.

In a preferred embodiment of the invention injection solutions, which are used for intravenous administrations, have a buffer capacity of up to 5 mVal/l, preferably up to 1 mVal/l, particularly from 0.3 mVal/1 up to 0.1 mVal/l, especially up to 0.05 mVal/l.

Furthermore, the ready-to-inject vein-compatible injection solution advantageously has a titration basicity which is as low as possible, namely from 10 to 0.05 mmol/l, especially from 1.0 to 0.05 mmol/l.

Preferred limits for the titration basicity of the injection solutions for successful intravenous administration are up to 10 ml, preferably up to 5 ml, especially up to 3 ml and particularly up to 1 ml, of a 0.1N NaOH solution. This corresponds to a titration basicity up to 1 mmol/l, especially up to 0.3 mmol/l, particularly up to 0.1 mmol/l.

The titration acidity or basicity is generally defined as that amount of acid or alkali which is required to adjust the pH value in a solution having a volume of 1 l to the pH value of blood (about 7.0 to 7.4).

The method for the determination of the titration basicity is carried out in an analogous manner to the determination of the buffer capacity by starting from the finished administerable injection solution or infusion solution and determining that amount of base which is required to adjust the pH value of the solution to about 7.0 to 7.4.

The production of the injection solution in accordance with the invention is preferably effected by suspending the active substance in the organic solvent with part of the required water and dissolving the active substance by the addition of the appropriate amount of buffer substance. Thereafter, the solution is, if necessary, adjusted to the desired pH value of 4.0 to 7.4 by the addition of small amounts of alkali. The antioxidant and the agent which binds heavy metal ions are added in dissolved form, the injection solution is optionally provided with additional additives to adjust the isotonicity and made up to the final volume with water.

In order to achieve a reduction in the oxygen content of the injection solution in accordance with the invention, continuous gasification with nitrogen is preferably carried out during the production of the injection solution batch. The nitrogen gasification is continued not only during the sterile filtration, but also when the injection solution is drawn from the ampoule.

Of course, as an alternative the isolated carvedilol salt can also be used directly. The thus-obtained solution is filtered over a sterile filter having a pore diameter of 0.2 $\mu$m and thereafter filled into ampoules on an automatic ampoule filling machine while gassing with nitrogen and sterilized in an autoclave at 121° C. for 20 minutes. The ampoules are usually filled under nitrogen and can be stored at room temperature for at least 3 years without the occurrence of turbidity and without the active substance being chemically changed to a significant extent.

Having regard to the low buffer capacity and low titration basicity, the injection solutions in accordance with the invention have a very good vein tolerance and do not lead to significant pH changes at the injection site, so that an undiluted administration is possible, whereby the buffer capacity of the solutions should be lower than 5 mVal/ml solution, i.e. the pH value is brought to a pH value of 7 to 7.5 by the addition of a corresponding amount of 0.1N sodium hydroxide solution.

The solutions in accordance with the invention are ready-to-inject and can be injected directly. It is, however, likewise possible to admix them with an isotonic glucose or saline solution and to infuse.

The invention is illustrated in more detail in the following Examples.

Examples of Carvedilol Injection Solutions (in each Case for 1000 Ampoules)

EXAMPLE 1

| | |
|---|---|
| Carvedilol | 5.00 g |
| Acetic acid 100% | 2.00 g |
| Polyethylene glycol (macrogol 400) | 500.00 g |
| Methionine | 10.00 g |
| Titriplex III | 0.50 g |
| Water for injection ad | 5.00 l |

2.5 l of water for injection are placed in a vessel of sufficient size which is provided with a stirrer and macrogol is dissolved therein while stirring and under $N_2$ gasification. The carvedilol is suspended in the mixture while stirring vigorously and dissolved by the addition of acetic acid. The pH value is adjusted to 4.4 to 4.8 with 1N NaOH, methionine and Titriplex III are dissolved and the mixture is made up with water for injection to the final volume.

The solution is filtered over a 0.2 $\mu$m membrane filter or filter candle, filled into ampoules on a suitable filling machine under $N_2$ gasification and sterilized for 20 minutes at 121° C. in a steam sterilizer.

EXAMPLE 2

| | |
|---|---|
| Carvedilol | 5.00 g |
| Acetic acid | 2.00 g |
| Propylene glycol | 600.00 g |
| Methionine | 10.00 g |
| Titriplex III | 0.50 g |
| Water for injection ad | 5.00 l |

2.5 l of water for injection are placed in a vessel of sufficient size which is provided with a stirrer and propylene glycol is dissolved therein while stirring and under $N_2$ gasification. The carvedilol is suspended in the mixture while stirring vigorously and dissolved by the addition of acetic acid. The pH value is adjusted to 4.4 to 4.8 with 1N NaOH, methionine and Titriplex III are dissolved and the mixture is made up with water for injection to the final volume.

The solution is filtered over a 0.2 μm membrane filter or filter candle, filled into ampoules on a suitable filling machine under $N_2$ gasification and sterilized for 20 minutes at 121° C. in a steam sterilizer.

EXAMPLE 3

| | |
|---|---|
| Carvedilol | 5.00 g |
| Malic acid | 2.00 g |
| Polyethylene glycol (macrogol 400) | 500.00 g |
| Methionine | 10.00 g |
| Titriplex III | 0.50 g |
| Water for injection ad | 5.00 l |

2.5 l of water for injection are placed in a vessel of sufficient size which is provided with a stirrer and macrogol is dissolved therein while stirring and under $N_2$ gasification. The carvedilol is suspended in the mixture while stirring vigorously and dissolved by the addition of malic acid. The pH value is adjusted to 4.4 to 4.8 with 1N NaOH, methionine and Titriplex III are dissolved and the mixture is made up with water for injection to the final volume.

The solution is filtered over a 0.2 μm membrane filter or filter candle, filled into ampoules on a suitable filling machine under $N_2$ gasification and sterilized for 20 minutes at 121° C. in a steam sterilizer.

EXAMPLE 4

| | |
|---|---|
| Carvedilol | 5.00 g |
| Citric acid $H_2O$ | 2.00 g |
| Polyethylene glycol (macrogol 400) | 500.00 g |
| Methionine | 10.00 g |
| Titriplex III | 0.50 g |
| Water for injection ad | 5.00 l |

2.5 l of water for injection are placed in a vessel of sufficient size which is provided with a stirrer and macrogol is dissolved therein while stirring and under $N_2$ gasification. The carvedilol is suspended in the mixture while stirring vigorously and dissolved by the addition of citric acid. The pH value is adjusted to 4.4 to 4.8 with 1N NaOH, methionine and Titriplex III are dissolved and the mixture is made up with water for injection to the final volume.

The solution is filtered over a 0.2 μm membrane filter or filter candle, filled into ampoules on a suitable filling machine under $N_2$ gasification and sterilized for 20 minutes at 121° C. in a steam sterilizer.

EXAMPLE 5

| | |
|---|---|
| Carvedilol | 5.00 g |
| Malic acid | 2.00 g |
| Propylene glycol | 600.00 g |
| Methionine | 10.00 g |
| Titriplex III | 0.50 g |
| Water for injection ad | 5.00 l |

2.5 l of water for injection are placed in a vessel of sufficient size which is provided with a stirrer and propylene glycol is dissolved therein while stirring and under $N_2$ gasification. The carvedilol is suspended in the mixture while stirring vigorously and dissolved by the addition of malic acid. The pH value is adjusted to 4.4 to 4.8 with 1N NaOH, methionine and Titriplex III are dissolved and the mixture is made up with water for injection to the final volume.

The solution is filtered over a 0.2 μm membrane filter or filter candle, filled into ampoules on a suitable filling machine under $N_2$ gasification and sterilized for 20 minutes at 121° C. in a steam sterilizer.

EXAMPLE 6

| | |
|---|---|
| Carvedilol | 5.00 g |
| Malic acid | 2.00 g |
| Torasemide | 10.00 g |
| Poylethylene glycol (macrogol 400) | 500.00 g |
| Methionine | 10.00 g |
| Titriplex III | 0.50 g |
| Water for injection ad | 5.00 l |

2.5 l of water for injection are placed in a vessel of sufficient size which is provided with a stirrer and macrogol is dissolved therein while stirring and under $N_2$ gasification. The carvedilol is suspended in the mixture while stirring vigorously and dissolved by the addition of malic acid and the toresamide. The pH value is adjusted to 4.4 to 4.8 with 1N NaOH, methionine and Titriplex III are dissolved and the mixture is made up with water for injection to the final volume.

The solution is filtered over a 0.2 μm membrane filter or filter candle, filled into ampoules on a suitable filling machine under $N_2$ gasification and sterilized for 20 minutes at 121° C. in a steam sterilizer.

EXAMPLE 7

| | |
|---|---|
| Carvedilol | 5.00 g |
| Malic acid | 2.00 g |
| Azosemide | 1.00 g |
| Polyethylene glycol (macrogol 400) | 500.00 g |
| Methionine | 10.00 g |
| Edetic acid disodium salt (Titriplex III) | 0.50 g |
| Water for injection ad | 5.00 l |

2.5 l of water for injection are placed in a vessel of sufficient size which is provided with a stirrer and macrogol is dissolved therein while stirring and under $N_2$ gasification. The carvedilol is suspended in the mixture while stirring vigorously and dissolved by the addition of malic acid and the azosemide. The pH value is adjusted to 4.4 to 4.8 with 1N NaOH, methionine and Titriplex III are dissolved and the mixture is made up with water for injection to the final volume.

The solution is filtered over a 0.2 μm membrane filter or filter candle, filled into ampoules on a suitable filling machine under $N_2$ gasification and sterilized for 20 minutes at 121° C. in a steam sterilizer.

What is claimed is:

1. A ready-to-use injection solution comprising carvedilol, or its pharmacologically harmless salts as the active substance, said injection solution at a concentration of 1–5 mg/ml, a physiologically compatible buffer having a pH value of 4 to 7.2, a water-soluble organic solvent in an amount of 5 to 25 wt %, an antioxidant and an agent which binds heavy metal ions.

2. An injection solution according to claim 1, wherein the buffer is a sodium, potassium or ammonium salt of a weak acid and/or a loop diuretic or its sodium or potassium salt.

3. An injection solution according to claim 2, wherein the loop diuretic is torasemide, azosemide or furosemide.

4. An injection according to claim 1, which has a buffer capacity of up to 5 mVal/l and a titration basicity from 10 mmol/l to 0.05 mmol/l.

5. An injection solution according to claim 4, wherein the buffer capacity is up to 1 mVal/l and the titration basicity is from 1.0 mmol/l to 0.05 mmol/l.

6. An injection solution according to claim 1, wherein the water-soluble organic solvent is polyethylene glycol, trimethylene glycol or ethanol.

7. An injection solution according to claim 6, wherein the water-soluble organic solvent is polyethylene glycol.

8. An injection solution according to claim 7, wherein the polyethylene glycol has a molecular weight of 100 to 1,500.

9. An injection solution according to claim 7, wherein the polyethylene glycol has a molecular weight of 200 to 600.

10. An injection solution according to claim 1, wherein the antioxidant is an inorganic or organic sulphur compound or ascorbate.

11. An injection solution according to claim 10, wherein the organic sulphur compound is methionine or sodium disulphide.

12. An injection solution according to claim 1, wherein the agent which binds heavy metal ions is a complex former.

13. An injection solution according to claim 12, wherein the complex former is EDTA or its disodium salt.

14. An injection solution according to claim 1, further comprising additives for adjusting isotonicity.

15. A process for the production of a ready-to-use injection solution in accordance with claim 1, which process comprises suspending the active substance in the water-soluble organic solvent and dissolving it by the addition of an appropriate amount of buffer; adjusting the solution to the desired pH value between 4.0 to 7.4 by the addition of alkali, adding the antioxidant and the agent which binds heavy metal ions in dissolved form, adding additives for adjustment of the isotonicity and adding water sufficient to reach a final volume.

* * * * *